(12) United States Patent
Keiper et al.

(10) Patent No.: US 9,414,868 B1
(45) Date of Patent: Aug. 16, 2016

(54) GUIDE PLACEMENT DEVICE AND METHOD OF USE

(71) Applicant: Spinelogik, Inc., Eugene, OR (US)

(72) Inventors: Glenn Keiper, Eugene, OR (US); Jeffrey Paris Wensel, Eugene, OR (US)

(73) Assignee: SPINELOGIK, INC., Eugene, OR (US)

( * ) Notice: Subject to any disclaimer, the term of this patent is extended or adjusted under 35 U.S.C. 154(b) by 0 days.

(21) Appl. No.: 13/842,275

(22) Filed: Mar. 15, 2013

Related U.S. Application Data

(60) Provisional application No. 61/737,079, filed on Dec. 13, 2012.

(51) Int. Cl.
*A61B 17/88* (2006.01)
*A61B 17/70* (2006.01)

(52) U.S. Cl.
CPC .................................. *A61B 17/7083* (2013.01)

(58) Field of Classification Search
CPC ........... A61B 17/1615; A61B 17/8897; A61B 17/17; A61B 17/1697; A61B 17/7083
USPC ...... 606/279, 86 R, 190–194, 104, 80, 96–99
See application file for complete search history.

(56) References Cited

U.S. PATENT DOCUMENTS

| | | | | |
|---|---|---|---|---|
| 3,430,345 A | * | 3/1969 | Abreu | 433/144 |
| 4,573,448 A | * | 3/1986 | Kambin | 606/170 |
| 5,354,299 A | * | 10/1994 | Coleman | 606/916 |
| 5,374,270 A | * | 12/1994 | McGuire et al. | 606/80 |
| 2002/0087161 A1 | * | 7/2002 | Randall et al. | 606/73 |
| 2004/0199166 A1 | * | 10/2004 | Schmieding | A61B 17/1617 606/79 |
| 2007/0027522 A1 | * | 2/2007 | Chang et al. | 623/1.11 |
| 2007/0219635 A1 | | 9/2007 | Mathieu et al. | |
| 2008/0200915 A1 | * | 8/2008 | Globerman et al. | 606/80 |

FOREIGN PATENT DOCUMENTS

EP    2289433 A2  *  3/2011  ............. A61B 17/16

* cited by examiner

*Primary Examiner* — Mary Hoffman
*Assistant Examiner* — Tara R Carter
(74) *Attorney, Agent, or Firm* — Adeli LLP

(57) ABSTRACT

Some embodiments of the invention provide an apparatus that secures, at a particular location in a bone, a guidance needle for guiding a cannulated device into the bone at the particular location. In some embodiments, the apparatus includes a tap for advancing the guidance needle into the bone. The guidance needle is used to guide the cannulated device to the particular location in the bone. In some embodiments, the tap is threaded and used to create a threaded guide path to further direct the placement of the cannulated device within the bone.

16 Claims, 11 Drawing Sheets

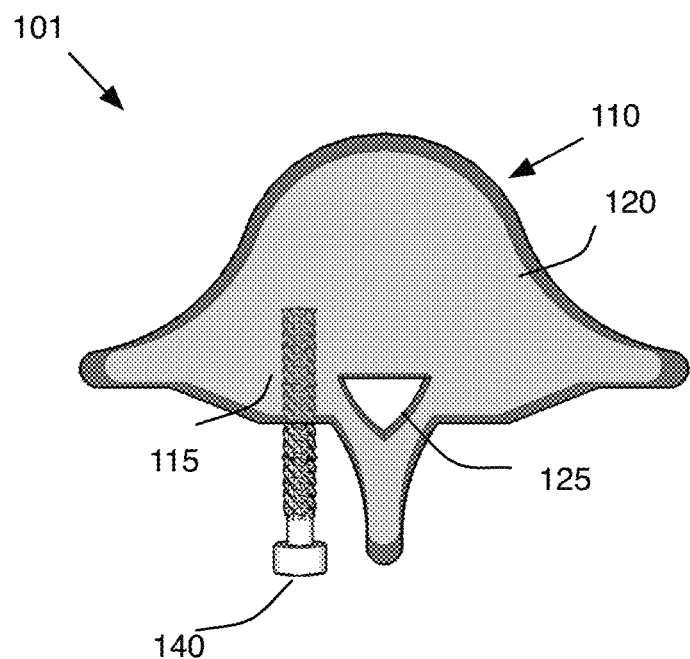
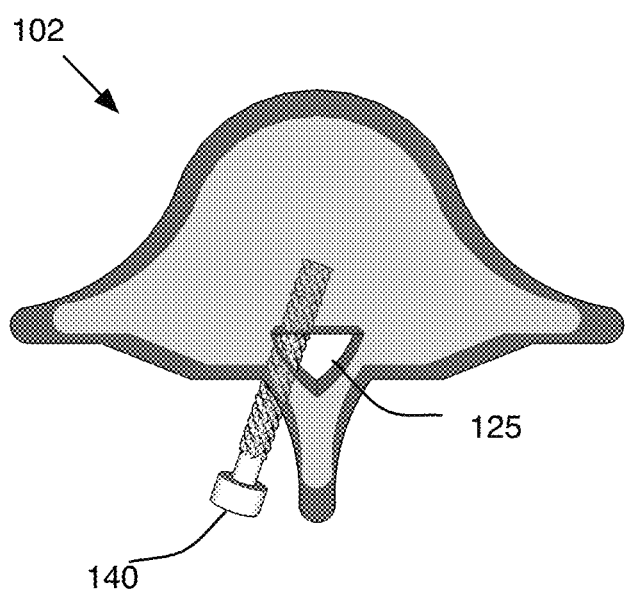
Figure 1

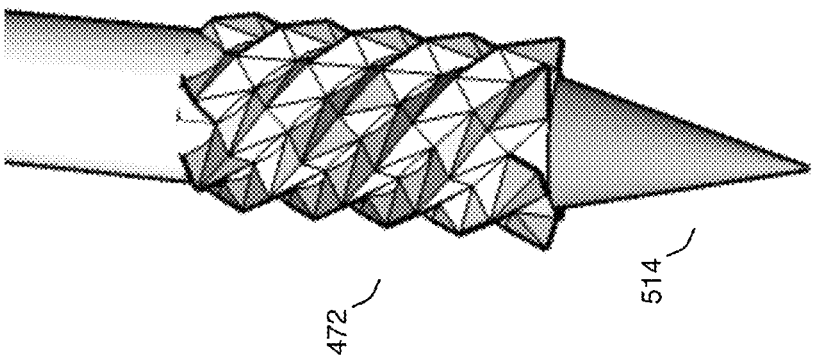
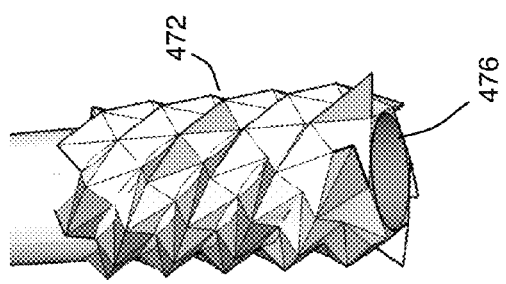
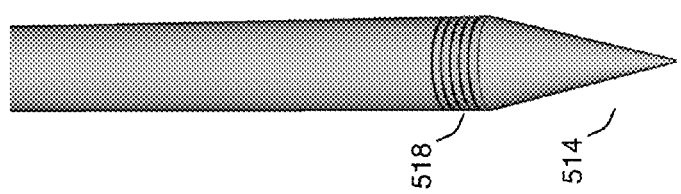
*Figure 8*

GUIDE PLACEMENT DEVICE AND METHOD OF USE

CLAIM OF BENEFIT TO PRIOR APPLICATION

This present Application claims the benefit of U.S. Provisional Patent Application 61/737,079 filed Dec. 13, 2012. U.S. Provisional Patent Application 61/737,079 is incorporated herein by reference.

BACKGROUND OF THE INVENTION

Lumbar spinal fusion surgeries are performed hundreds of thousands of times each year. When a particular vertebral segment causes pain for a patient, the surgery prevents movement at the particular vertebral segment to decrease the pain. The surgery fuses adjacent vertebral segments together with bone grafts. In order for these grafts to heal, the adjacent vertebral segments must be kept in place.

In order to keep the adjacent vertebral segments in place, pedicle screws and control rods are used to stabilize the vertebral segments. The pedicle screws are screwed into the pedicle of each of the adjacent vertebral segments. A control rod is then passed through the heads of the pedicle screws, preventing movement between the adjacent vertebral segments.

In order to place the pedicle screws, a needle is inserted to a desired location on the pedicle. A guide wire is then passed through the needle to the pedicle. The guide wire may only be inserted a few millimeters into the pedicle. The guide wire is then used to pass various instruments to the desired location. These instruments are used to dilate the opening and drill a guide path. The guide wire is also used to guide the pedicle screw to the desired location so that it can be screwed into the pedicle.

With such a weak purchase of only a few millimeters in the pedicle and with multiple operations which need to be performed over the guide wire, the guide wire will often slip from the desired location. When the wire slips, the surgeon may lose orientation/surgical landmarks and delay access for screw placement. The guide wire may slip multiple times during a single procedure.

In some cases, the unsecured placement of the guide wire results in misplacement of the pedicle screw. Misplacing the pedicle screw could result in significant harm to the patient. FIG. 1 illustrates examples of the placement of lumbar pedicle screws, including an example of the misplacement of a pedicle screw. The two scenarios 101-102 show a vertebral segment 110 and a pedicle screw 140. Both scenarios 101-102 show a top-down, cross-section view of the vertebral segment 110. The vertebral segment 110 shows pedicle 115, a vertebral body 120, and a spinal canal 125. Nerve bundles (not shown) run through the spinal canal 125 between the vertebral bodies along the spine.

The first scenario 101 illustrates pedicle screw 140 placed correctly through the pedicle 115 into the vertebral body 120. The pedicle screw 140 is placed straight through the pedicle 115 without interfering with the spinal canal 125.

The second scenario 102 shows the pedicle screw 140 placed incorrectly. Pedicle screws may be misplaced when a guide wire slips due to a weak purchase on the bony surface of the posterior elements just posterior to the pedicle, either losing the desired entry location to the pedicle or altering the direction of penetration for the pedicle screws. Because of the angle and missed location at which the pedicle screw 140 is placed, the screw passes through a part of the spinal canal 125 and interferes with nerve bundles (not shown) in the spinal canal. Incorrect placement of the pedicle screws can have potentially serious consequences, such as damaging the nerves or weakening the structure of the vertebral segment.

FIG. 2 illustrates the use of pedicle screws in a spinal fusion operation. FIG. 2 shows pedicle screws 240 inserted into vertebral bodies 220 in two views 201 and 202. View 201 shows a dorsal view of the placement of the pedicle screws 240 and the control rods 242 in the vertebral bodies 220. View 202 shows the same placement of the pedicle screws 240 and the control rods 242 in the vertebral bodies 220 from a side angle. Control rods are shown through the heads 244 of the pedicle screws 240, preventing excessive movement between the vertebral bodies.

SUMMARY OF THE INVENTION

Some embodiments of the invention provide an apparatus that secures, at a particular location in a bone, a guidance needle for guiding a cannulated device into the bone at the particular location. In some embodiments, the apparatus includes a tap for advancing the guidance needle into the bone. The guidance needle is used to guide the cannulated device to the particular location in the bone. In some embodiments, the tap is threaded and used to create a threaded guide path to further direct the placement of the cannulated device within the bone.

The guidance needle is for (1) embedding in the bone and (2) guiding a cannulated device to the particular location in the bone. In some embodiments, the guidance needle is further configured to secure the guidance needle within the bone. For example, the distal end of the guidance needle may be configured with securing members that help to secure the guidance needle in the bone. In some embodiments, the securing members are backfacing ridges that provide resistance to removal of the guidance needle from the bone. Other embodiments use different types of securing members to secure the guidance needle in the bone, such as adhesives.

In some embodiments, the apparatus includes a handle for driving and rotating the apparatus. The handle is configured to secure the tap and the guidance needle. The handle is configured to hold the proximal ends of the threaded tap and the guidance needle, providing support for the insertion of the threaded tap and the guidance needle in the bone. In some embodiments, the handle has two cavities, one for supporting the guidance needle and the other for supporting the threaded tap. In some embodiments, the handle has coupling elements in the first cavity for coupling with corresponding coupling elements of the threaded tap. By having two cavities, the handle allows the guidance needle to extend beyond the end of the threaded tap. In some embodiments, a medical practitioner taps the extended end of the guidance needle using a medical hammer to secure the distal end of the guidance needle in the bone.

Some embodiments of the invention provide a method for placing a guidance needle into a bone. The guidance needle is for guiding a cannulated device, such as a pedicle screw, to a particular location of a bone, such as a pedicle of a vertebral segment. The method (1) secures a cannulated tap in a bone, (2) taps a guidance needle through the tap into the bone and (3) removes the cannulated tap without removing the guidance needle. In some embodiments, the method is performed by a medical practitioner. In some embodiments, the medical practitioner may use the method to place a guidance needle in a pedicle of a vertebral segment in order to place a pedicle screw in the vertebral segment. In some embodiments, the method further comprises assembling the guidance needle and the cannulated tap before inserting the cannulated tap into the body. The assembled device is then inserted into the body to secure the cannulated tap in the bone.

The preceding Summary is intended to serve as a brief introduction to some embodiments of the invention. It is not meant to be an introduction or overview of all of the inventive subject matter disclosed in this document. The Detailed Description that follows and the Drawings that are referred to in the Detailed Description will further describe the embodiments described in the Summary as well as other embodiments. Accordingly, to understand all the embodiments described by this document, a full review of the Summary, Detailed Description and the Drawings is needed. Moreover, the claimed subject matters are not to be limited by the illustrative details in the Summary, Detailed Description and the Drawing, because the claimed subject matters can be embodied in other specific forms without departing from the spirit of the subject matters.

BRIEF DESCRIPTION OF THE DRAWINGS

The novel features of the invention are set forth in the appended claims. However, for purpose of explanation, several embodiments of the invention are set forth in the following figures.

FIG. 1 illustrates the placement of the lumbar pedicle screw in a pedicle.

FIG. 8 illustrates a more detailed view of the distal end of the device after the proper insertion of the guidance needle into the threaded tap.

DETAILED DESCRIPTION

In the following description, numerous details are set forth to provide a better understanding of the various embodiments of the invention. However, one of reasonable skill in the art will realize that the invention may be practiced without the use of the specific details presented herein. In some instances of describing the invention, well-known structures may be omitted or shown in block diagram form to avoid obscuring the description of the invention with unnecessary detail. Therefore, the examples provided herein for description and clarification should not be interpreted as in any way limiting the language of the claims.

I. Guide Placement Device

Figure 2:
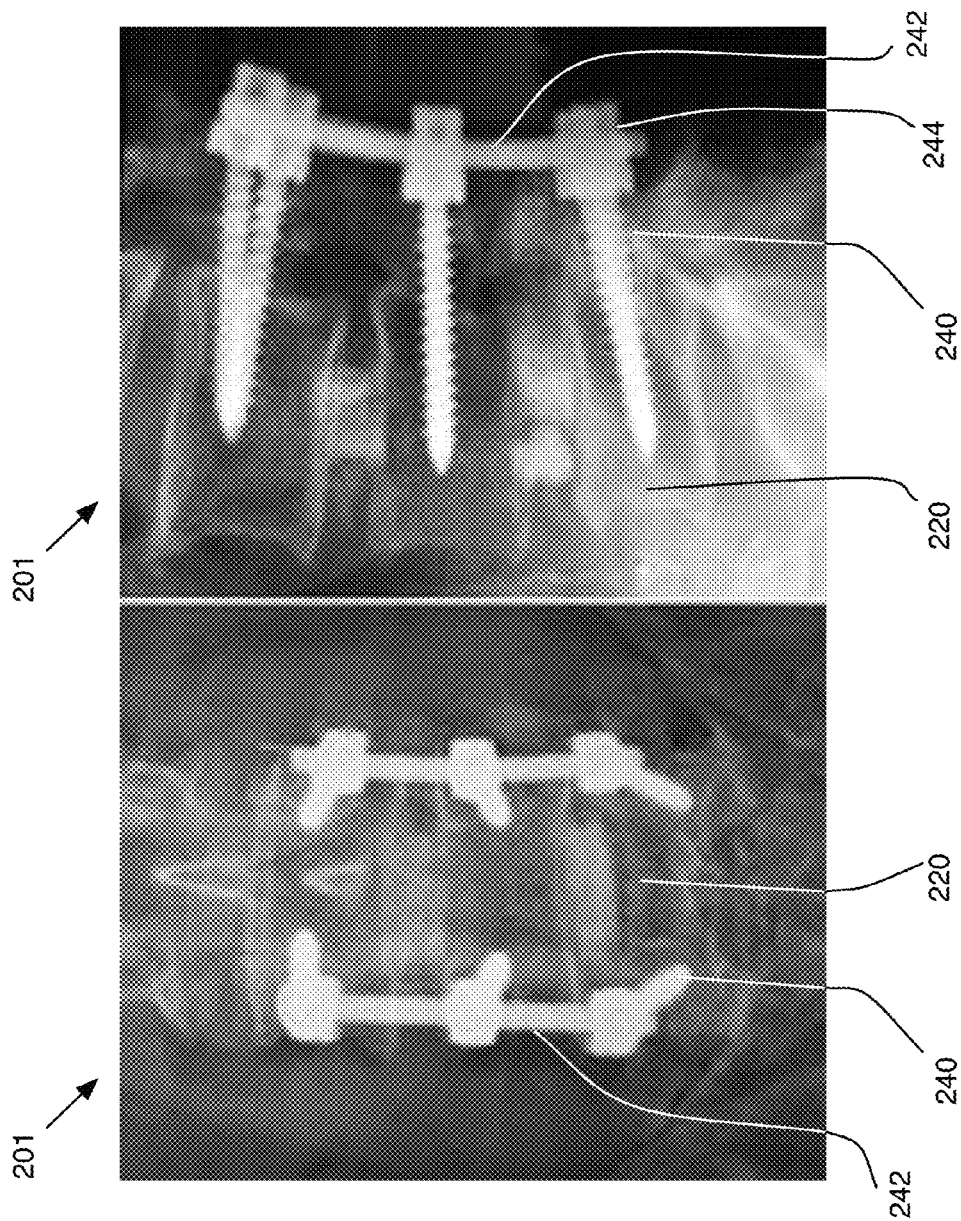
FIG. 2 illustrates the use of pedicle screws in a spinal fusion operation.
Figure 3:
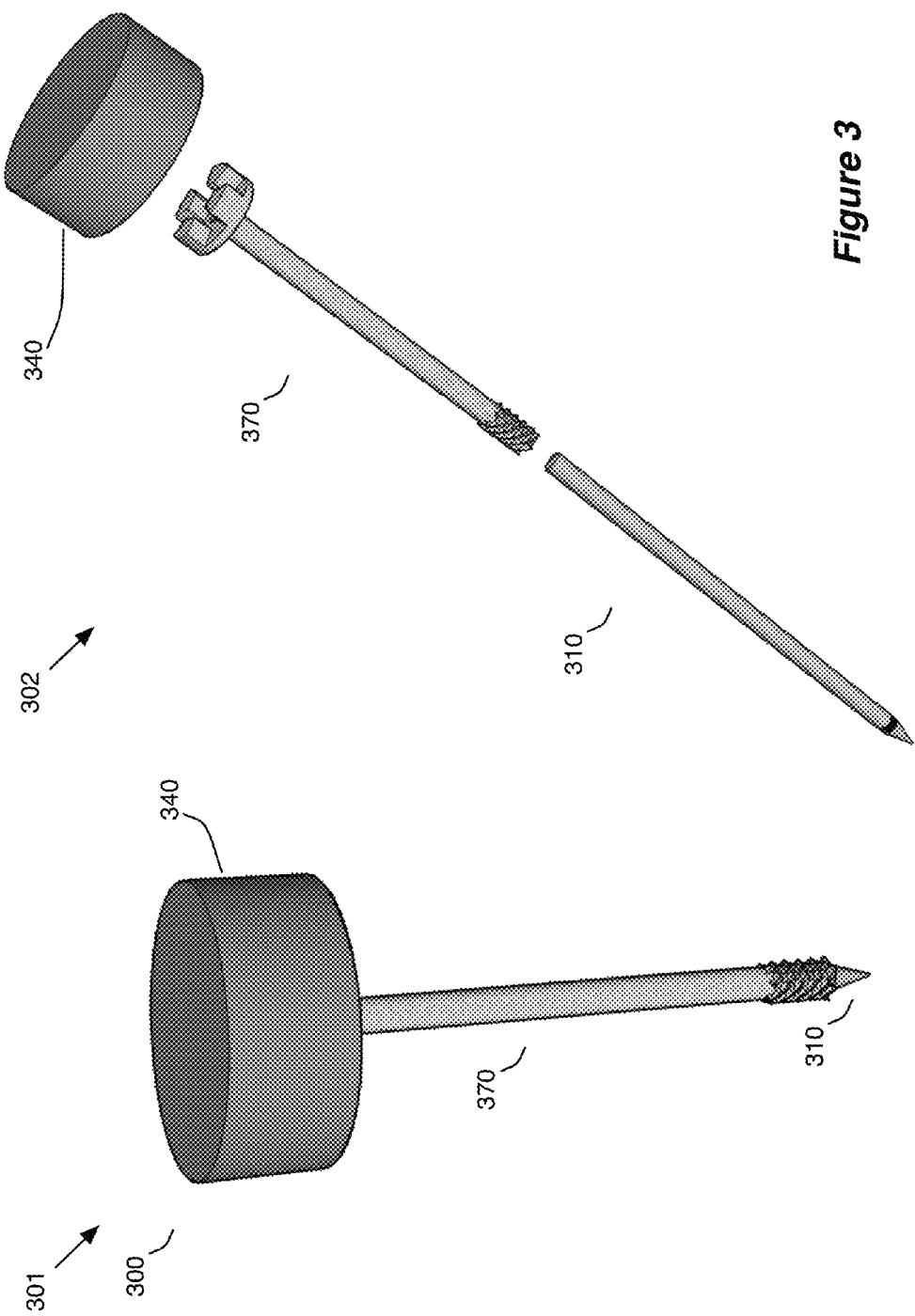
FIG. 3 illustrates the assembled apparatus of some embodiments.

FIG. 3 illustrates a guide placement device 300 of some embodiments. View 301 shows an assembled view of the guide placement device including the handle 340, the threaded tap 370, and the guidance needle 310. View 302 shows a disassembled view of the guide placement device 300 including the handle 340, the threaded tap 370, and the guidance needle 310. The guide placement device 300 secures the guidance needle 310 at a particular location in a bone so that a cannulated device (not shown) can be passed over the guidance needle 310 to the particular location in the bone. The guide placement device 300 includes the guidance needle 310 and the threaded tap 370. The threaded tap 370 is used to initially secure the guidance needle 310 within the bone. In some embodiments, the threaded tap 370 also creates a threaded guide path which can be used to guide the placement of the cannulated device within the bone. The guidance needle 310 is for guiding the cannulated device, such as a pedicle screw, to a desired location in a bone, such as a pedicle of a vertebral body. A medical practitioner may use the guide placement device 300 during a spinal fusion surgery to place pedicle screws (not shown) into the vertebral bodies in order to secure the vertebral bodies with control rods (not shown).

The guidance needle 310, the handle 340, and the threaded tap 370 are further described by reference to FIGS. 4-6 below. The parts of the threaded tap 370 are illustrated in further detail from different perspectives in FIG. 4. The parts of the guidance needle 310 are illustrated in further detail from different perspectives in FIG. 5. The parts of the handle 340 are illustrated in further detail from different perspectives in FIG. 6.

A. Threaded Tap

Figure 4:
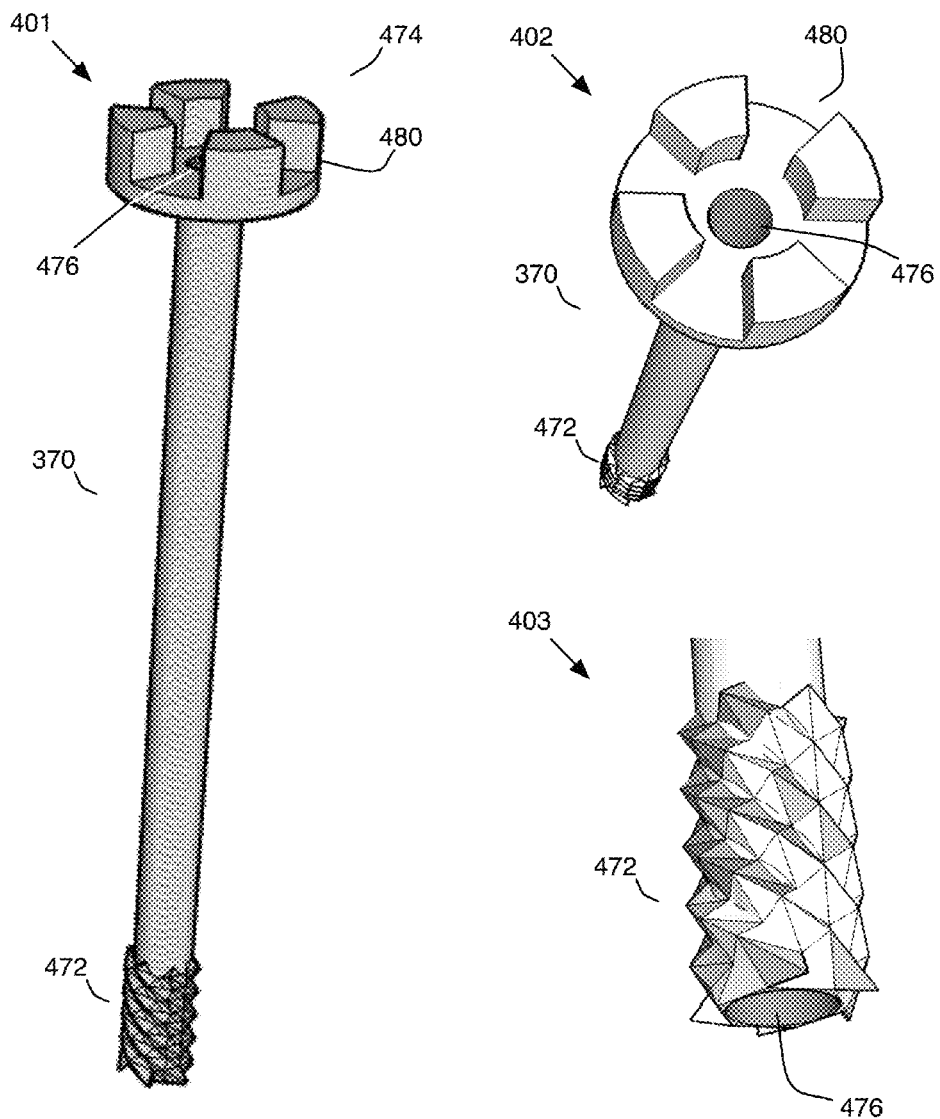
FIG. 4 illustrates different views of the threaded tap of some embodiments.

FIG. 4 illustrates different views of the threaded tap 370 of FIG. 3. View 401 is a side view of the threaded tap 370. View 402 is a top down view of the threaded tap 370. View 403 is a magnified view of distal end of the threaded tap 370. The threaded tap 370 is for enlarging a path to the bone and creating a threaded guide path cavity in the bone which assists with proper alignment and placement of a threaded device (not shown) such as a pedicle screw in the bone in some embodiments. The threaded tap 370 includes a threaded distal end 472, a proximal end 474, a channel 476, and a coupling segment 480. In some embodiments, the threaded tap 370 can be composed of any number of materials, such as metals (e.g., stainless steel, titanium, or nitinol), various polymers (e.g., PMMA or polyetheretherketone), carbon fiber, etc.

The threaded distal end 472 of the threaded tap 370 is configured to advance the threaded tap 370 into a bone, creating a threaded cavity when the threads of the threaded distal end 472 are pressed and rotated into the bone. In some embodiments, the threads of the threaded distal end 472 are slightly smaller and shallower than the threads of a threaded, cannulated apparatus, such as a standard pedicle screw, allowing for a secure fit when the cannulated apparatus is screwed into the threaded cavity created by the threaded distal end 472.

The proximal end 474 is where the guidance needle is inserted into the channel 476 of the threaded tap 370. In some embodiments, the channel 476 runs through the length of the threaded tap 370 and is used to hold the guidance needle while a medical practitioner places the guidance needle into the pedicle.

In some embodiments, the proximal end includes the coupling segment 480 for interfacing with a handle. The coupling segment 480 joins with corresponding coupling members of the handle. The joining allows a medical practitioner to push a guidance needle (not shown) into the pedicle and drive the threads of the threaded tap 370 into the pedicle by rotating and/or pressing the handle. In some embodiments, the joining may include latching, interlocking, coupling, or screwing the coupling segment 480 and coupling members together. In some embodiments, rather than a coupling segment 480, an alternative mechanism for temporarily securing the guidance needle into the handle, such as an adhesive, is used.

The guidance needle traverses the channel 476. The guidance needle is inserted into the channel when the device is assembled and then slides out of the channel 476 after the guidance needle has been secured into the bone. The inner diameter of the channel 476 will match closely with the diameter of the guidance needle, allowing the guidance needle to pass through, but also providing resistance. The resistance prevents the guidance needle from falling out of the threaded tap 370, but is not so great that the threaded tap 370 cannot be pulled back over the guidance needle once the needle is secured in the pedicle. In some embodiments, the resistance of the threaded tap 370 is less than resistance provided by securing members of the guidance needle to secure the distal end of the guidance needle within the bone. In some embodiments, the outer diameter of the shaft of the threaded tap 370 is between 3-5 millimeters.

B. Guidance Needle

Figure 5:
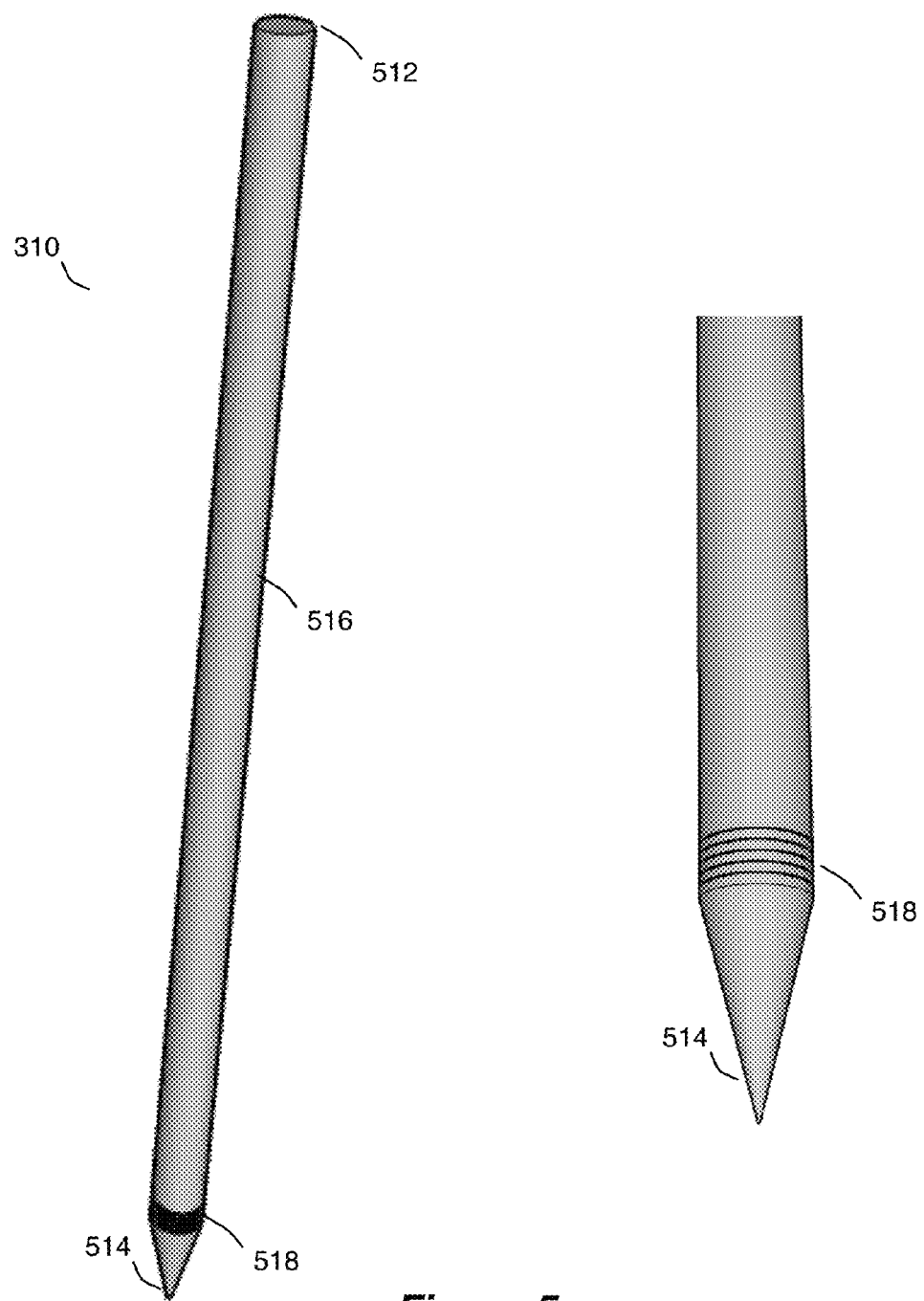
FIG. 5 illustrates different views of the guidance needle of some embodiments.

FIG. 5 illustrates different views of the guidance needle 310 of FIG. 3. The guidance needle 310 is used to guide a cannulated apparatus (not shown), such as a pedicle screw, into the pedicle of a patient. In some embodiments, the guidance needle has a diameter of approximate 1-2 millimeters, allowing other cannulated apparatuses (e.g., pedicle screws, dilators, the threaded tap, etc.) to be passed over the guidance needle. When the guidance needle 310 is secured in place, a channel of a cannulated apparatus (not shown) is passed over the guidance needle 310 so that the cannulated apparatus can be guided to a desired location on the bone along the guidance needle before being screwed into the bone. The guidance needle 310 includes an extended proximal end 512, a pointed distal end 514, a shaft 516, and securing mechanism 518.

The extended proximal end 512 is extended relative to the threaded tap. The shaft 516 of the guidance needle 310 is longer than the threaded tap and when the device is assembled, the extended proximal end 512 protrudes from a proximal end of the threaded tap. The shaft 516 of the guidance needle 310 may be between 10 and 20 centimeters long, in some embodiments. The extended proximal end 512, in some embodiments, extends beyond the proximal end of the threaded tap by approximately 2 centimeters. The extended proximal end 512 is configured to extend from the threaded tap so that, once the guidance needle 310 is initially inserted into the bone, the extended proximal end 512 can be tapped or otherwise advanced, driving the guidance needle 310 deeper into the bone. The extended proximal end 512, along with the shaft 516 can pass through the channel 476 of the threaded tap as the guidance needle 310 is tapped into the bone. When the guide placement device is assembled, the extended proximal end 512 fits into a cavity of the handle. The extended proximal end 512 is described and illustrated in further detail below with reference to FIGS. 7 and 9.

The pointed distal end 514 is configured for inserting into the bone. The pointed distal end 514 extends from the distal end of the threaded tap when the guide placement device is assembled. The pointed distal end 514, in some embodiments, is made of a metal (e.g., stainless steel, titanium, or nitinol) or another rigid material which can penetrate the bone.

The securing mechanism 518, illustrated as lines, is located near the pointed distal end 514 and is configured to secure the guidance needle 310 in the bone. When the guidance needle 310 is driven into the pedicle area, the securing mechanism 518 provides resistance against removal of the guidance needle 310, securing the guidance needle 310 in the bone yet also allowing for removal of the guidance needle 310 when necessary. In some embodiments, the securing mechanism 518 is a set of back-facing ridges or other structures (e.g., adhesives, textured surfaces, etc.) for providing resistance against removal or inadvertent shifting of the guidance needle 310. In some embodiments, the securing mechanism 518 is strongly secured to the bone and removing the securing mechanism 518 includes removing the part of the bone to which the securing mechanism 518 is secured.

C. Handle

Figure 6:
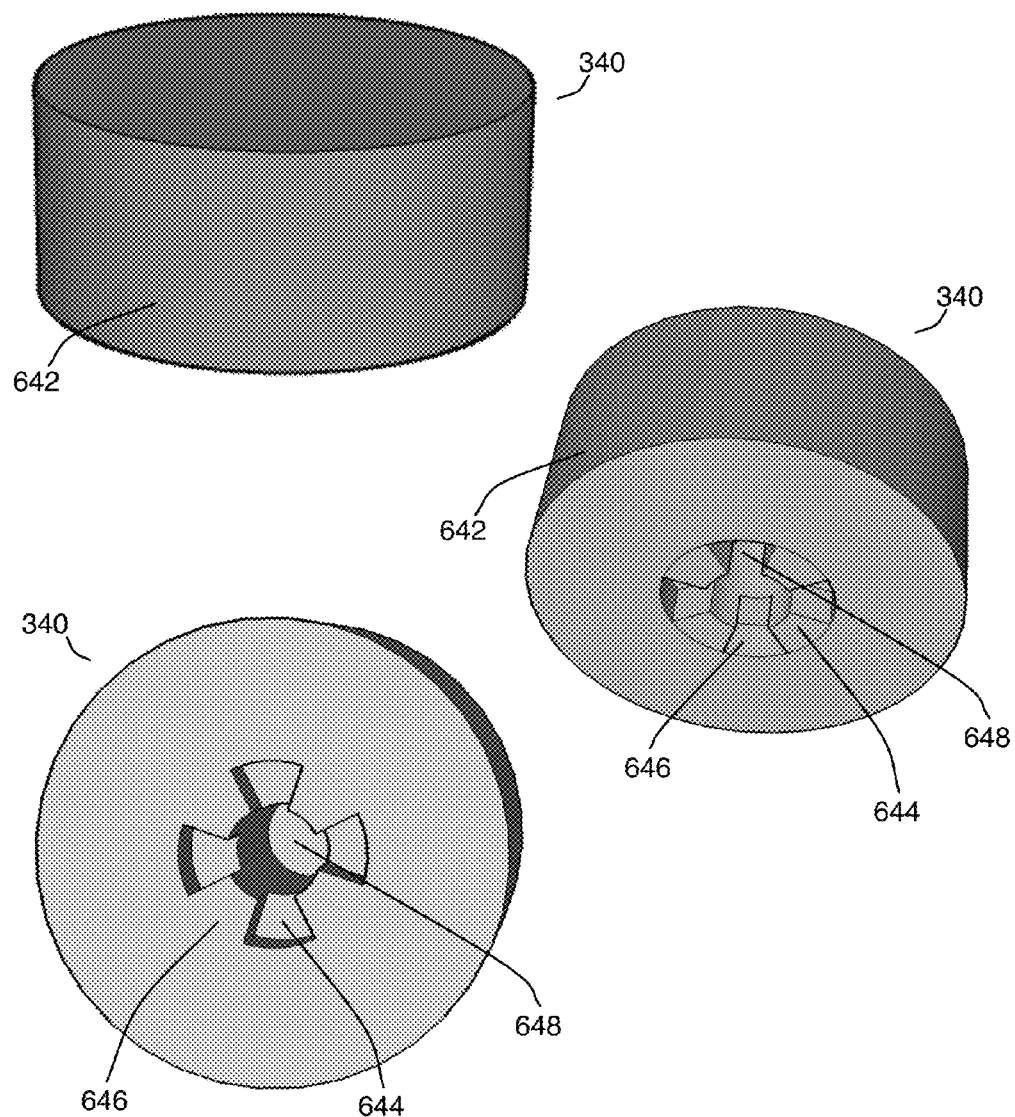
FIG. 6 illustrates different views of the handle of some embodiments.

FIG. 6 illustrates different views of the handle 340 of FIG. 3. The handle 340 is used to drive the guidance needle and the threaded tap into the bone. The handle includes a side edge 642 for gripping the handle 340, a first cavity 644 with coupling members 646 for engaging the threaded tap, and a second cavity 648 to hold the extended proximal end of the guidance needle.

The handle 340 as shown is a rounded circular shape, but may be other shapes (e.g., rectangular, hexagonal, etc.), which allows for a controlling grip of the device in other embodiments. In some embodiments, the handle 340 is approximately 5 centimeters in diameter, allowing for a comfortable grip of the handle 340. The side edge(s) of the handle 340 provide grip for rotating, pushing and pulling the handle 340. The grip may be provided by the material used to make the handle 340, textures on the side edges, or other designs to facilitate a proper grip.

The first cavity 644 engages the proximal end of the threaded tap. The first cavity is configured to secure the threaded tap in the handle 340. The circumference of the first cavity is similar to the proximal end of the threaded tap, in some embodiments, to allow for a secure fit between the threaded tap and the handle 340. The first cavity has coupling members 646 which are structured to interact with the coupling segment of the threaded tap to secure the threaded tap in the handle 340. The coupling members 646, in some embodiments, are teeth that interlock with teeth on the coupling segment of the threaded tap. In some embodiments, the coupling segment 646 is configured to securely couple the handle 340 to the threaded tap to prevent rotation of the coupling segment 646 apart from the handle 340. However, in some embodiments, even while securely coupled rotationally, the handle 340 can be removed from the threaded tap by pulling on the handle 340 away from the threaded tap.

The second cavity 648 holds the extended proximal end of the guidance needle. The second cavity 648 has a smaller circumference than the first cavity 644 and reaches deeper into the handle 340 than the first cavity 644. The second cavity 648 is configured to support the extended proximal end of the guidance needle, preventing the guidance needle from slipping toward the proximal end of the threaded tap when the device is pushed into the pedicle. In some embodiments, the guidance needle is flexible and the second cavity 648 is closed-ended. The second cavity 648 provides support for the guidance needle to push the guidance needle into the pedicle.

In some embodiments, the handle 340 can be composed of any number of materials, such as metals (e.g., stainless steel, titanium, or nitinol), various polymers (e.g., PMMA or polyetheretherketone), carbon fiber, etc. In some embodiments, the guide placement device does not include a separate handle and is instead used by manipulating the threaded tap and guidance needle directly.

II. Assembly of the Guide Placement Device

Figure 7:
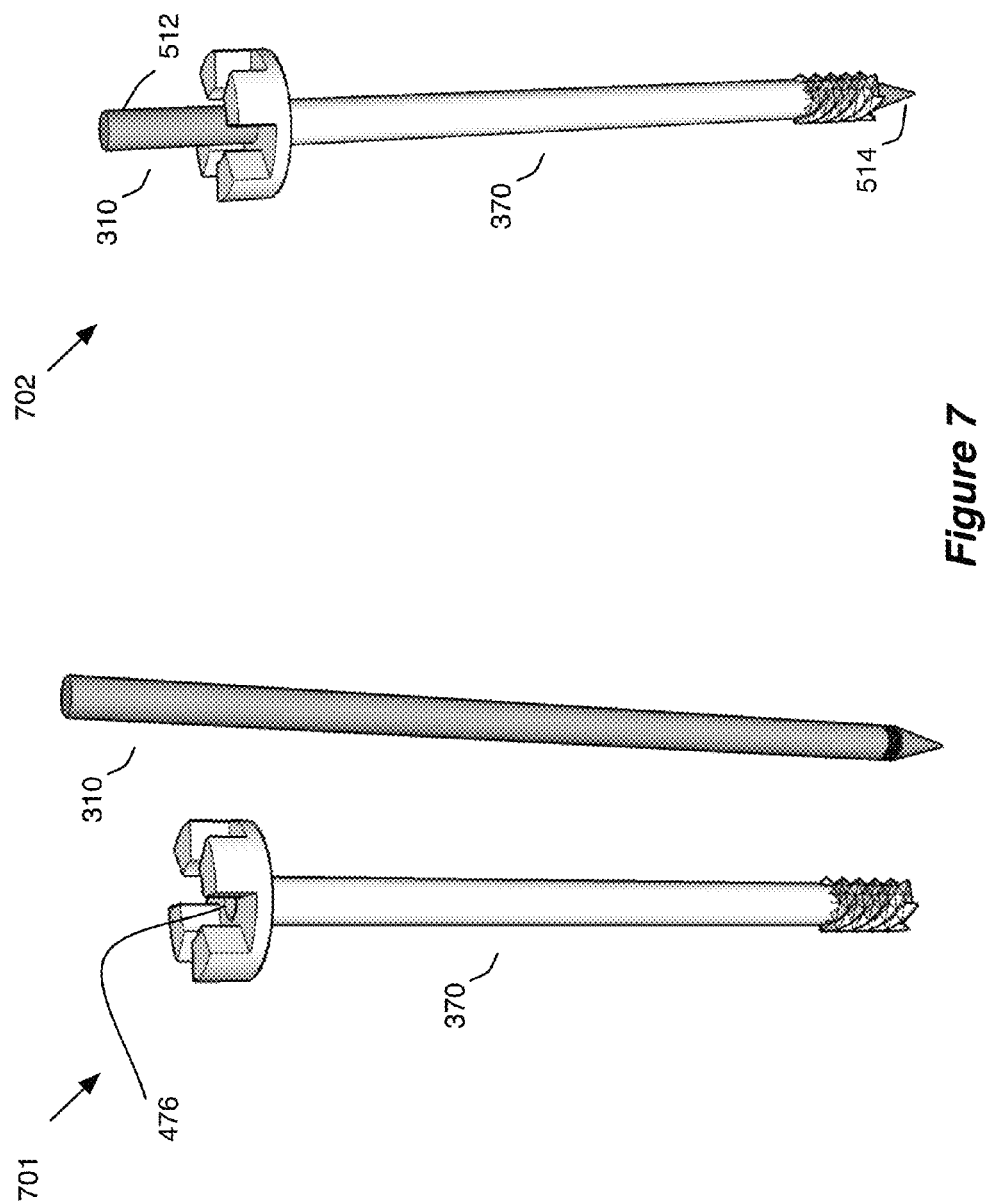
FIG. 7 shows the initial assembly of the guidance needle and the threaded tap.

The assembly of the guide placement device 300 is described with reference to FIGS. 7-9. FIG. 7 shows the initial assembly of the guidance needle 310 and the threaded tap 370 in two stages 701-702. Stage 701 shows the guidance needle 310 and the threaded tap 370 and channel 476 of the threaded tap before the guidance needle 310 and threaded tap 370 are assembled. Stage 702 shows the assembled guidance needle and threaded tap. The guidance needle 310 is inserted into the channel 476 of the threaded tap 370 to produce the assembled guidance needle and threaded tap shown in stage 702. As can be seen in stage 702, when the guidance needle and threaded tap are assembled, the extended proximal end 512 of the guidance needle 310 extends out of the proximal end of the threaded tap 370. In some embodiments, the extended proximal end 512 of the guidance needle 310 is configured to fit into the second cavity of the handle (not shown). The pointed distal end 514 of the guidance needle 310 extends out of the distal end of the threaded tap 370. In some embodiments, the pointed distal end 514 of the guidance needle 310 is used to mark a particular location for the cannulated device.

FIG. 8 illustrates a more detailed view of the distal end of the guide placement device after the proper insertion of the guidance needle 310 into the threaded tap 370. When assembled, the pointed end 514 of guidance needle 310 extends from the threaded end 472 of the threaded tap 370, but the securing mechanism 518 remains within the channel 476 of the threaded tap 370. In some embodiments, the securing mechanism 518 is exposed and secured to the bone when the guidance needle 310 is driven into the bone. This process is described in further detail below with reference to FIG. 11.

Figure 9:
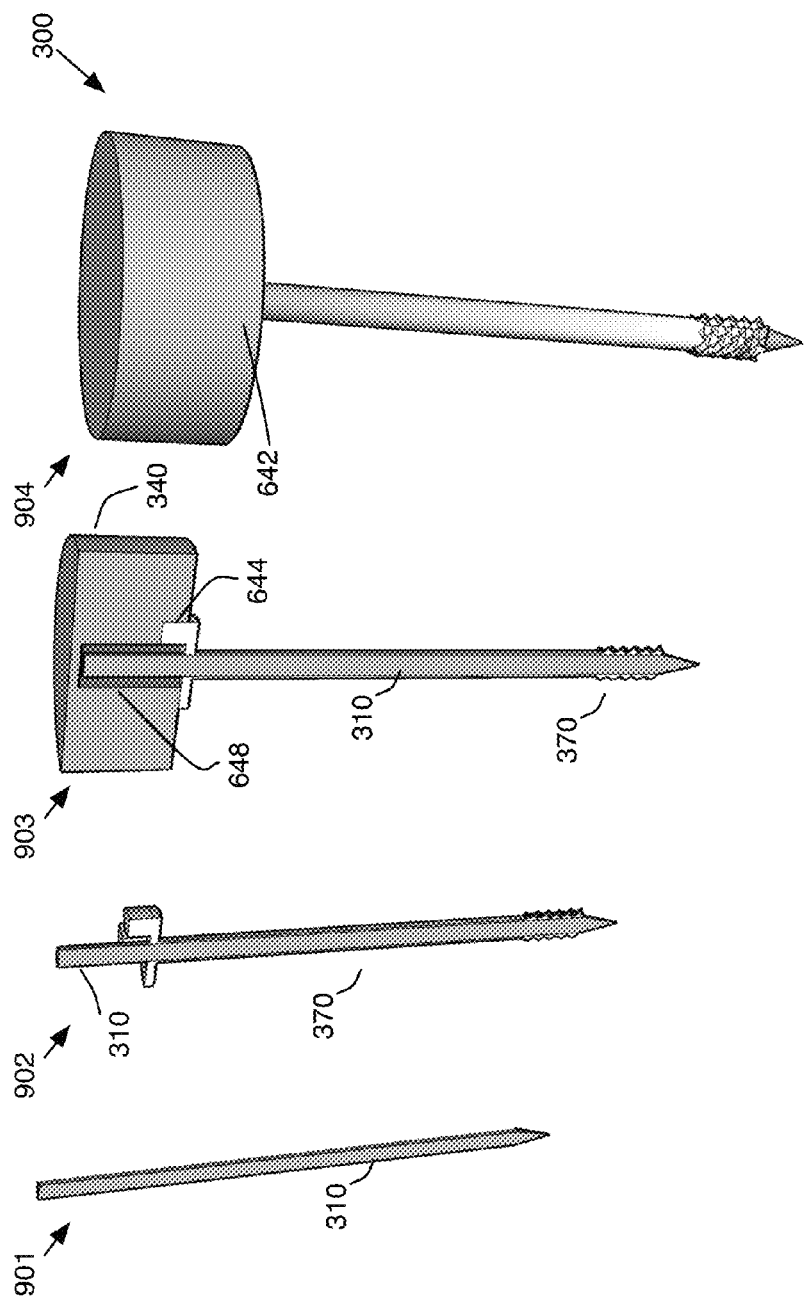
FIG. 9 shows a cutaway view of the full assembly of the guide placement device of some embodiments.

FIG. 9 shows four views 901-904 of a cutaway of the full assembly of the guide placement device 300 of some embodiments. View 901 shows a cutaway of the guidance needle 310. View 902 shows a cutaway of the assembled guidance needle and threaded tap shown in stage 702 of FIG. 7 with the guidance needle traversing the channel of the threaded tap. View 903 shows a cutaway of the fully assembled guide placement device 300 after the coupling members 646 of the handle 340 have been fitted with the coupling segment 480 on the proximal end of the threaded tap 370. As shown, the fitted coupling members 646 and coupling segment 480 fit into the first cavity 644 of the handle 340. The extended proximal end 512 of the guidance needle 310 fits into the second cavity 648 of the handle. View 904 shows the fully assembled guide placement device 300 without a cutaway.

III. Method for Using the Guide Placement Device

Figure 10:
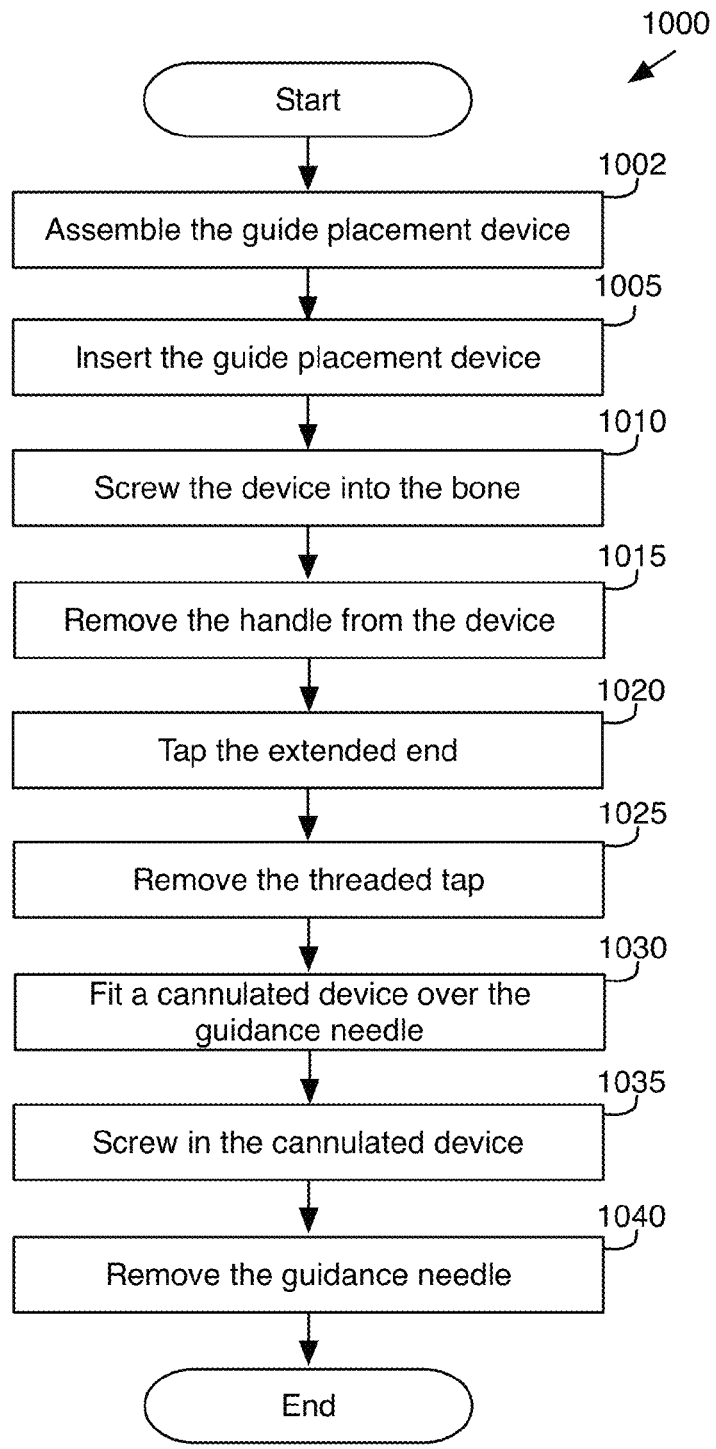
FIG. 10 conceptually illustrates a process for using the guide placement device.

FIG. 10 conceptually illustrates the process 1000 for the placement of a guide placement device in a pedicle of a patient by a machine or a medical practitioner. Proper placement of the guide placement device allows for accurate placement of cannulated apparatuses by the medical practitioner. The process 1000 will be described with reference to FIG. 11.

Figure 11:
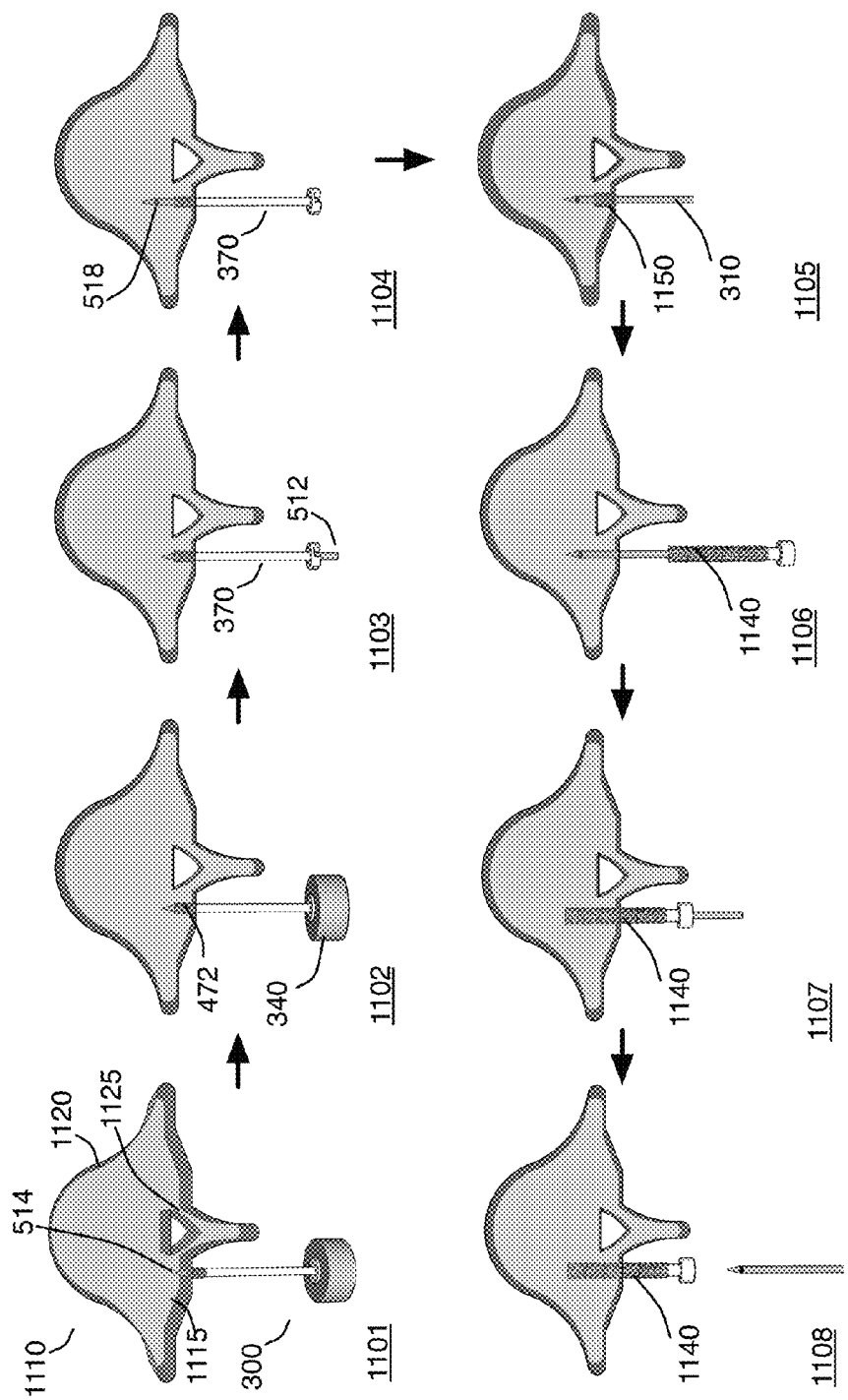
FIG. 11 illustrates placing pedicle screws using the guide placement device.

FIG. 11 illustrates the placement of the guide placement device 300 in eight stages 1101-1108. FIG. 11 shows a vertebral segment 1110 similar to the vertebral segment 110 of FIG. 1 and a guide placement device 300. The vertebral segment 1110 shows pedicle 1115, vertebral body 1120, and spinal canal 1125. Although the placement of the guide placement device is described with reference to a vertebral segment, the invention is not limited to such a particular use.

The process 1000 begins by assembling (at 1002) the guide placement device, if the device is not already assembled as described in Section II. In some embodiments, assembling the guide placement device includes inserting the guidance needle into the threaded tap until the pointed end extends out of the threaded, distal end of the threaded tap. The proximal end of the combined threaded tap and the extended end of the guidance needle are then fitted into the handle, coupling the coupling segment of the threaded tap with the coupling members of the handle, and fitting the extended proximal end of the guidance needle into the second cavity of the handle.

The process 1000 inserts (at 1005) the distal end of the guide placement device at a particular location of the pedicle until the threaded distal end of the threaded tap comes into contact with the pedicle. The medical practitioner may push the pointed distal end of the guidance needle into the pedicle by tapping, pushing, and/or twisting against the handle of the device. The first stage 1101 of FIG. 11 shows that the pointed distal end 514 of the guidance needle of the guide placement device 300 has been pressed into the pedicle 1115 of the vertebral segment 1110.

Next, the process 1000 rotates (at 1010) the handle of the device, screwing the device into the pedicle. Screwing the device into the pedicle stabilizes the device for subsequent steps. In addition, screwing the device into the pedicle creates a threaded guide path which can later be used to guide the insertion of a pedicle screw into the pedicle. The second stage 1102 of FIG. 11 shows the guide placement device 300 after the threaded distal end 472 of the threaded tap has been screwed into the pedicle 1115.

The process 1000 then removes (at 1015) the handle from the device, exposing the extended proximal end of the guidance needle. The handle can be readily removed (e.g., by pulling or twisting) from the threaded tap in some embodiments without dislodging the guidance needle or the threaded tap. The third stage 1103 of FIG. 11 shows that the handle 340 has been removed from the device 300 and that the extended proximal end 512 of the guidance needle is protruding from the proximal end of the threaded tap 370.

The process 1000 taps (at 1020) the extended proximal end using a medical hammer, for example. The tapping pushes the pointed, distal end of the guidance needle into the pedicle beyond the end of the threaded tap. By advancing the guidance needle into the pedicle, the securing mechanism 518 of the guidance needle is able to secure itself to the pedicle in some embodiments. The fourth stage 1104 of FIG. 11 shows that the guidance needle 310 has been driven into the pedicle 1115, with the pointed distal end 514 of the guidance needle 310 now extending beyond the distal end 472 of the threaded tap 370, allowing the securing mechanism 518 to secure the guidance needle 310 into the pedicle 1115. At this point, the threaded tap 370 can be removed without disengaging the guidance needle 310 from the pedicle 1115 which is secured in the pedicle by the securing mechanism 518 of the guidance needle. In some embodiments, the securing mechanism is a set of back-facing ridges or an adhesive that provides resistance against removal of the guidance needle.

The process 1000 removes (at 1025) the threaded tap by unscrewing the threads from the threaded guide path and sliding it back over the proximal end of the guidance needle 310. Since the guidance needle has the securing mechanism (e.g., the back-facing ridges, adhesives, textured surface) to hold it in place, the threaded tap can slide over the guidance needle without pulling it out of the pedicle. The fifth stage 1105 of FIG. 11 shows that the threaded tap 370 has been removed, leaving a threaded guide path 1150 and the guidance needle in the pedicle 1115.

The process 1000 then fits (at 1030) a pedicle screw 1140 (or other cannulated apparatus) over the guidance needle 310 through a channel in the pedicle screw, guiding the pedicle screw 1140 to the threaded guide path 1150 at the particular location of the pedicle. The sixth stage 1106 of FIG. 11 shows the pedicle screw 1120 being threaded over the guidance needle 310.

The process 1000 screws (at 1035) in the pedicle screw 1140, using the threaded guide path 1150 as a guide to maintain the desired orientation for the pedicle screw. The seventh stage 1107 of FIG. 11 shows that the pedicle screw 1120 is screwed into the pedicle 1115. The pedicle screw is screwed into the pedicle through the threaded guide path and into the vertebral segment. The pedicle screw, in some embodiments, is screwed in over the securing mechanism 518 of the guidance needle, releasing the hold of the securing mechanism on the surrounding bone.

Once the pedicle screw is secured in the desired position, the process removes (at 1040) the guidance needle 1110. The eighth stage 1108 of FIG. 11 shows that the guidance needle 1010 has been removed through the channel of the pedicle screw. The process 1000 then ends.

The process 1000 allows for more accurate placement of the pedicle screws while preventing guide wires from becoming dislodged. By screwing the device into the pedicle, the device begins a guide path for the pedicle screw. Creating the guide path with the handle and the threaded tap during the placement of the guidance needle enables a medical practitioner to easily control the direction of the guide path. Securing the guidance needle by tapping the guidance needle and the securing mechanism into the pedicle ensures a reliable path for the pedicle screw to the desired location in the pedicle.

We claim:

1. A method for placing a guidance needle comprising:
   assembling a guide placement device comprising a guidance needle, a cannulated guiding member, and a handle;
   using the handle of the assembled guide placement device to drive the cannulated guiding member into a bone in order to secure the cannulated guiding member in the bone;
   disassembling the guide placement device by removing the handle from the guide placement device after the cannulated guiding member is secure;
   tapping the guidance needle through the cannulated guiding member in order to affix the guidance needle into a portion of the bone; and
   removing the cannulated guiding member without removing the guidance needle from the bone.

2. The method of claim 1, wherein a distal end of the guidance needle comprises back-facing edges.

3. The method of claim 1, wherein the method further comprises:
   after removal of the cannulated guiding member, fitting a pedicle screw over the guidance needle in order to secure the pedicle screw into the bone; and
   once the pedicle screw is secured, releasing the guidance needle along with the portion of the bone from the particular bone.

4. An apparatus comprising:
   a guiding member configured to penetrate a bone, the guiding member comprising a channel and a guidance needle configured to pass through the channel and into the bone; and
   a removable handle connected to the guiding member that is configured to control the guiding member into the bone, the removable handle comprising a cavity on one side and a closed-end on an opposite side, wherein a proximal end of the guiding member is configured to fit into the cavity of the removable handle and removal of the removable handle exposes a proximal end of the guidance needle.

5. The apparatus of claim 4, wherein a distal end of the guiding member is threaded.

6. The apparatus of claim 4, wherein the guidance needle, when secured into the bone, is configured to guide a cannulated apparatus into the bone.

7. The apparatus of claim 6, wherein the cannulated apparatus comprises a threaded distal end.

8. The apparatus of claim 4, wherein a distal end of the guidance needle is configured to secure the guidance needle in the bone.

9. The apparatus of claim 4, wherein a shaft of the guidance needle is longer than the channel of the guiding member.

10. The apparatus of claim 4, wherein the guidance needle is exposed at least partially from the channel of the guiding member.

11. The apparatus of claim 4, wherein the guidance needle comprises a securing mechanism along a shaft of the guidance needle configured to affix the guidance needle into the bone.

12. The apparatus of claim 11, wherein the securing mechanism comprises back-facing edges that are configured to secure the guidance needle into the bone.

13. The apparatus of claim 4, wherein the cavity is a first cavity, wherein the removable handle further comprises a second cavity.

14. The apparatus of claim 13, wherein the guidance needle is configured to fit into the second cavity.

15. The apparatus of claim 13, wherein a proximal end of the first cavity opens to a distal end of the second cavity and a proximal end of the second cavity is the closed-end.

16. The apparatus of claim 13, wherein a distal end of the guidance needle aligns with a distal end of the guiding member when the proximal end of the guidance needle is fitted into the second cavity and the proximal end of the guiding member is fitted into the first cavity.

\* \* \* \* \*